US007563761B2

(12) United States Patent
Braun et al.

(10) Patent No.: US 7,563,761 B2
(45) Date of Patent: Jul. 21, 2009

(54) PNA CONJUGATE FOR THE TREATMENT OF DISEASES ASSOCIATED WITH HIV

(75) Inventors: Klaus Braun, Sandhausen (DE); Waldemar Waldeck, Laudenbach (DE); Rudiger Pipkorn, Heidelberg (DE); Isabell Braun, Colbe-Burgeln (DE); Jurgen Debus, Stettfeld (DE)

(73) Assignee: Deutsches Krebsforschungszentrum Stiftung des Offentlichen Rechts (DE)

( * ) Notice: Subject to any disclaimer, the term of this patent is extended or adjusted under 35 U.S.C. 154(b) by 192 days.

(21) Appl. No.: 10/483,654

(22) PCT Filed: Jul. 12, 2002

(86) PCT No.: PCT/DE02/02564

§ 371 (c)(1),
(2), (4) Date: Apr. 21, 2004

(87) PCT Pub. No.: WO03/006065

PCT Pub. Date: Jan. 23, 2003

(65) Prior Publication Data

US 2004/0220095 A1 Nov. 4, 2004

(30) Foreign Application Priority Data

Jul. 12, 2001 (DE) ................................ 101 33 307

(51) Int. Cl.
*C07H 21/00* (2006.01)
*A61K 38/16* (2006.01)

(52) U.S. Cl. ............................... 514/2; 514/12; 514/13; 514/42; 514/44; 530/326; 536/23.1

(58) Field of Classification Search ....................... None
See application file for complete search history.

(56) References Cited

U.S. PATENT DOCUMENTS 6,221,355 B1 4/2001 Dowdy
6,821,948 B1 * 11/2004 Braun et al. ................... 514/2

FOREIGN PATENT DOCUMENTS

| | | |
|---|---|---|
| WO | WO 98/40502 | 9/1998 |
| WO | WO 01/05432 | 1/2001 |
| WO | WO 03/015708 | 2/2003 |
| WO | WO 03/039438 | 3/2003 |
| WO | WO 03/040365 | 3/2003 |
| WO | WO 03/047631 | 6/2003 |

OTHER PUBLICATIONS

Braun et al. "Setting the stage for bech-to-bedside movment of anti-HIV RNA inhibitors-gene therapy for AIDS in macques" Frontiers in Bioscience, vol. 11, pp. 838-851, Jan. 2006.*

Gait et al. "Progress in anti-HIV structure based drug design." TIBTECH, vol. 13. pp. 430-438, Oct. 1995.*

Siliciano et al. 'A Long Term Latent Reservoir for HIV-1: Discovery ADN Clinical Implications.' J. of Antimicrob. Chemo. vol. 54, No. 1, pp. 6-9. Jul. 2004.*

Koppelhus U. et al., "Efficient In Vitro Inhibition of HIV-1 Gag Reverse Transcription by Peptide Nucleic Acid (PNA) at Minimal Ratios of PNA/RNA," Nucleic Acids Res. 25:2167-2173 (1997).*

Mayhood et al. "Inhibition of Tat-mediated transactivation of HIV-1 LTR transcription by polyamide nucleic acid targeted to TAR hairpin element." Biochemistry, 39, 11532-11539. 2000.*

Klaus Braun, et al.; A Biological Transporter for the Delivery of Peptide Nucleic Acids (PNAs) to the Nuclear Compartment of Living Cells; J. Mol. Biol., 2002 318, pp. 237-243.

R. Pipkorn, et al.; Peptide Carrier for Efficient Drug Transport Into Living Cells; Peptides the Wave of the Future, American Peptide Society, 2001, pp. 931-932.

Derossi, Daniele, et al.; Trojan peptides: the penetratin system for intracellular delivery; trends in Cell Biology, vol. 8, Feb. 1998, pp. 84-87.

Pardridge, William M., et al.; Vector-mediated delivery of a polyamide ("peptide") nucleic acid analogue through the blood-brain barrier in vivo, Proc. Natl. Acad. Sci. USA, vol. 92, Jun. 1995, pp. 5592-5596.

Hällbrink, Mattias et al.; Cargo delivery kinetics of cell-penetrating peptides; Biochimica et Biophysica Acta 1515, 2001, pp. 101-109.

Nielsen, Peter, E., et al. "Sequence-Selective Recognition of DNA by Strand Displacement with a Thymine-Substituted Polyamide." Science, vol. 254, (1991), pp. 1497-1500.

Pooga, Margus, et al. "Cell penetration by transportan." The FASEB Journal, vol. 12, (1998), pp. 67-77.

Merrifield, R. B. "Solid Phase Peptide Synthesis. I. The Synthesis of a Tetrapeptide." Journal of the American Chemical Society, vol. 85 (1963), pp. 2149-2154.

Rietsch, Arne, et al. "The Genetics of Disulfide Bond Metabolism." Annual Review of Genetics, vol. 32, (1998), pp. 163-184.

Shiramizu, B., et al. "Identification of a common clonal human immunodeficiency virus integration site in human immunodeficiency virus-associated lymphomas." Cancer Research, vol. 54, (1994), pp. 2069-2072.

Britten, R. J., et al. "Repeated Sequence in DNA." Science, vol. 161, (1968), pp. 529-540.

(Continued)

*Primary Examiner*—Anish Gupta
(74) *Attorney, Agent, or Firm*—Kelly K. Reynolds; Steven J. Hultquist; Intellectual Property/Technology Law

(57) ABSTRACT

The invention relates to peptide nucleic acid (PNA) conjugates which can be used for treating diseases correlated with HIV, wherein the peptide nucleic acid (PNA) inhibits the gene expression of HIV. The conjugates comprise the following components: (a) a transport mediator for the cell membrane, (b) an address protein or peptide for the import into the cell nucleus, and (c) a peptide nucleic acid (PNA) which is to be transported and can be hybridized with an HIV gene and can inhibit the expression of the HIV gene.

7 Claims, 13 Drawing Sheets

OTHER PUBLICATIONS

Cutrona, Giovanna, et al., Effects in live cells of a c-myc anti-gene PNA linked to a nuclear localization signal, Nature Biotechnology, Mar. 2000, pp. 300-303, vol. 18, No. 3.

Donahue, Robert E., et al., Reduction in SIV replication in rhesus macaques infused with autologous lymphocytes engineered with antiviral genes, Nature Medicine, Feb. 1998, pp. 181-186, vol. 4, No. 2.

Lee, Reaching, et al., Polyamide Nucleic Acid Targeted to the Primer Binding Site of the HIV-1 RNA Genome Blocks in Vitro HIV-1 Reverse . . . , Biochemistry, Jan. 20, 1998, pp. 900-910, vol. 37, No. 3.

McShan, W. Michael, et al., Inhibition of transcription of HIV-1 in infected human cells by oligodeoxynucleotides designed to form DNA triple helice, J. Biol. Chem., Mar. 15, 1992, pp. 5712-5721, vol. 267, No. 8.

Pooga, Margus, et al., PNA oligomers as tools for specific modulation of gene expression , Biomolecular Engineering, Jun. 2001, pp. 183-192, vol. 17, No. 6.

Ray, Arghya, et al., Peptide nucleic acid (PNA): its medical and biotechnical applications and promise for the future , FASEB J., Jun. 2000, pp. 1041-1060, vol. 14, No. 9.

* cited by examiner

```
LOCUS       HIVHXB2CG    9719 bp ss-
DEFINITION  Human immunodeficiency virus type 1 (HXB2), complete genome;
            HIV1/HTLV-III/LAV reference genome.
ACCESSION   K03455 M38432
VERSION     K03455.1  GI:1906382
KEYWORDS    TAR protein; acquired immune deficiency syndrome; complete enome;env
protein; gag protein; long terminal repeat (LTR); pol protein;polyprotein;
proviral gene; reverse transcriptase; transactivator.
SOURCE      Human immunodeficiency virus type 1.
FEATURES             Location/Qualifiers
     source          1..9719
                     /organism="Human immunodeficiency virus type 1"
                     /db_xref="taxon:11676"
                     /note="HTLV-III/LAV"
     LTR             1..634
                     /note="5' LTR"
     repeat_region   454..551
                     /note="R repeat 5' copy"
     mRNA            455..9635
                     /note="HXB2 genomic mRNA"
     prim_transcript 455..9635
                     /note="tat, trs, 27K subgenomic mRNA"
     intron          744..5777
                     /note="tat, trs, 27K mRNA intron 1"
     CDS             790..2292

BASE COUNT     3411 a   1772 c   2373 g   2163 t
ORIGIN
     TGGAAGGGCT AATTCACTCC CAACGAAGAC AAGATATCCT TGATCTGTGG ATCTACCACA      60
     CACAAGGCTA CTTCCCTGAT TAGCAGAACT ACACACCAGG GCCAGGGATC AGATATCCAC     120
     TGACCTTTGG ATGGTGCTAC AAGCTAGTAC CAGTTGAGCC AGAGAAGTTA GAAGAAGCCA     180
     ACAAAGGAGA GAACACCAGC TTGTTACACC CTGTGAGCCT GCATGGAATG GATGACCCGG     240
     AGAGAGAAGT GTTAGAGTGG AGGTTTGACA GCCGCCTAGC ATTTCATCAC ATGGCCCGAG     300
     AGCTGCATCC GGAGTACTTC AAGAACTGCT GACATCGAGC TTGCTACAAG GGACTTTCCG     360
     CTGGGGACTT TCCAGGGAGG CGTGGCCTGG GCGGGACTGG GGAGTGGCGA GCCCTCAGAT     420
     CCTGCATATA AGCAGCTGCT TTTTGCCTGT ACTGGGTCTC TCTGGTTAGA CCAGATCTGA     480
     GCCTGGGAGC TCTCTGGCTA ACTAGGGAAC CCACTGCTTA AGCCTCAATA AAGCTTGCCT     540
     TGAGTGCTTC AAGTAGTGTG TGCCCGTCTG TTGTGTGACT CTGGTAACTA GAGATCCCTC     600
     AGACCCTTTT AGTCAGTGTG GAAAATCTCT AGCAGTGGCG CCCGAACAGG GACCTGAAAG     660
     CGAAAGGGAA ACCAGAGGAG CTCTCTCGAC GCAGGACTCG GCTTGCTGAA GCGCGCACGG     720
     CAAGAGGCGA GGGGCGGCGA CTGGTGAGTA CGCCAAAAAT TTTGACTAGC GGAGGCTAGA     780
     AGGAGAGAGA TGGGTGCGAG AGCGTCAGTA TTAAGCGGGG GAGAATTAGA TCGATGGGAA     840
     AAAATTCGGT TAAGGCCAGG GGGAAAGAAA AAATATAAAT TAAAACATAT AGTATGGGCA     900
     AGCAGGGAGC TAGAACGATT CGCAGTTAAT CCTGGCCTGT TAGAAACATC AGAAGGCTGT     960
     AGACAAATAC TGGGACAGCT ACAACCATCC CTTCAGACAG GATCAGAAGA ACTTAGATCA    1020
     TTATATAATA CAGTAGCAAC CCTCTATTGT GTGCATCAAA GGATAGAGAT AAAAGACACC    1080
     AAGGAAGCTT TAGACAAGAT AGAGGAAGAG CAAAACAAAA GTAAGAAAAA AGCACAGCAA    1140
     GCAGCAGCTG ACACAGGACA CAGCAATCAG GTCAGCCAAA ATTACCCTAT AGTGCAGAAC    1200
     ATCCAGGGGC AAATGGTACA TCAGGCCATA TCACCTAGAA CTTTAAATGC ATGGGTAAAA    1260
     GTAGTAGAAG AGAAGGCTTT CAGCCCAGAA GTGATACCCA TGTTTTCAGC ATTATCAGAA    1320
     GGAGCCACCC CACAAGATTT AAACACCATG CTAAACACAG TGGGGGGACA TCAAGCAGCC    1380
     ATGCAAATGT TAAAAGAGAC CATCAATGAG GAAGCTGCAG AATGGGATAG AGTGCATCCA    1440
     GTGCATGCAG GGCCTATTGC ACCAGGCCAG ATGAGAGAAC CAAGGGGAAG TGACATAGCA    1500
     GGAACTACTA GTACCCTTCA GGAACAAATA GGATGGATGA CAAATAATCC ACCTATCCCA    1560
     GTAGGAGAAA TTTATAAAAG ATGGATAATC CTGGGATTAA ATAAAATAGT AAGAATGTAT    1620
     AGCCCTACCA GCATTCTGGA CATAAGACAA GGACCAAAGG AACCCTTTAG AGACTATGTA    1680
     GACCGGTTCT ATAAAACTCT AAGAGCCGAG CAAGCTTCAC AGGAGGTAAA AAATTGGATG    1740
     ACAGAAACCT TGTTGGTCCA AAATGCGAAC CCAGATTGTA AGACTATTTT AAAAGCATTG    1800
     GGACCAGCGG CTACACTAGA AGAAATGATG ACAGCATGTC AGGGAGTAGG AGGACCCGGC    1860
     CATAAGGCAA GAGTTTTGGC TGAAGCAATG AGCCAAGTAA CAAATTCAGC TACCATAATG    1920
     ATGCAGAGAG GCAATTTTAG GAACCAAAGA AAGATTGTTA AGTGTTTCAA TTGTGGCAAA    1980
     GAAGGGCACA CAGCCAGAAA TTGCAGGGCC CCTAGGAAAA AGGGCTGTTG GAAATGTGGA    2040
     AAGGAAGGAC ACCAAATGAA AGATTGTACT GAGAGACAGG CTAATTTTTT AGGGAAGATC    2100
     TGGCCTTCCT ACAAGGGAAG GCCAGGGAAT TTTCTTCAGA GCAGACCAGA GCCAACAGCC    2160
     CCACCAGAAG AGAGCTTCAG GTCTGGGGTA GAGACAACAA CTCCCCCTCA GAAGCAGGAG    2220
     CCGATAGACA AGGAACTGTA TCCTTTAACT TCCCTCAGGT CACTCTTTGG CAACGACCCC    2280
     TCGTCACAAT AAAGATAGGG GGGCAACTAA AGGAAGCTCT ATTAGATACA GGAGCAGATG    2340
     ATACAGTATT AGAAGAAATG AGTTTGCCAG GAAGATGGAA ACCAAAAATG ATAGGGGGAA    2400
     TTGGAGGTTT TATCAAAGTA AGACAGTATG ATCAGATACT CATAGAAATC TGTGGACATA    2460
```

Fig. 2

```
                                      .         :         .         :         .         :         .         :
HIUU70276                                        G-CCTGGCCATAAAGCAAGAATTTTGGCTGAGGCAATGAGCC
HIUU70291     CATGTCGGGGAGTGGGGAGGACCTAGCCACAAAGCCAGAGTGTTGGCTGAGGCAATGAGCC
HIUU70281     CATGTCASGGAGTGGG-GGACCCGGCCATAAAGCAAGAGTTTTGGCTGAAGCAATGAGCC
HIVU70290                             CATAANGCAAGAGTTTTGGCTGAAGCAATGAGCC
HIUU70292             AGTGGGAGGMCCCGGCCAMAAAGCAAGGGTTTTGGCGGAAGCAATGAGCC
HIVU70292             AGTGGGAGGMCCCGGCCAMAAAGCAAGGGTTTTGGCGGAAGCAATGAGCC

                                      .         :    ↓   PNA  ①               ↓   .         :         .
HIUU70276     AGGTAACAAATACRGCTG---TAATGATGCAGCGAAACAACTTTAAGGGT--CAAAGAAA
HIUU70291     AAGCAAATAATACA---AACATAATGATGCAGAGAAACAACTTTAAAGGC-CCTAA-AAG
HIUU70281     AAGTAACACCACCAGCTAACATAATGATGCAGAGAGGCAATTTTA--GGAACCAAAGAAA
HIVU70290     AAGTAACACAACCAGCTACCATAATGATGCAGAGAGGCAATTTTA--GGAACCAAAGAAA
HIUU70292     AAGTAACAAATTCACCTGCCATAATGATGCAGAGAGGCAATTTTA--GGAACCAAAGAAA
HIVU70292     AAGTAACAAATTCACCTGCCATAATGATGCAGAGAGGCAATTTTA--GGAACCAAAGAAA

                       .         :         .         :     ↓  PNA ②        ↓  .
HIUU70276     AATTATTAAATGTTTCAACTGTGGCANGGAGGGACACYTAGCAAAAAATTGCAGGGCCCC
HIUU70291     AATTATTAAATGTTTCAACTGTGGCAAGGAAGGGCACTTAGCCAGAAATTGCAGGGCCCC
HIUU70281     GACTGTTAAGTGTTTCAATTGTNNNDAAGAAGGGCAYATAGCCAAAAATTGCAGGGCCCC
HIVU70290     GACTGTTAAGTGTTTCAATTGBBBVAAAGAAGGGCACATAGCCAAAAATTGCAGGGCCCC
HIUU70292     AACTGTTAAGTGTTTCAATTGTGGCAAAGAAGGGCACATAGCCAAAAATTGCAGGGCCCC
HIVU70292     AACTGTTAAGTGTTTCAATTGTGGCAAAGAAGGGCACATAGCCAAAAATTGCAGGGCCCC

              ↓    PNA ③                    ↓     .         :
HIUU70276     TAGGDDGDDGGGTTGTTGGAAATGT---AA
HIUU70291     TAGGAAAAAAGGCTGTTGGAAATGTGGAAAGGAAGGAC
HIUU70281     TAGGAADAAGGGCTGTTGGAAATGT
HIVU70290     TAGGAAAAAGGGCTGTTGGAAATGTGGTAGGGAAGGACAC
HIUU70292     TAGGAAAAGGGGCTGTTGGAAATGTGGHAAGGAAGGAM
HIVU70292     TAGGAAAAGGGGCTGTTGGAAATGTGGHAAGGAAGGAM
                ↓                          ↓
```

① ATTAC*TAC*GTC*TC*TC*C*GTT

② TATC*GGTTTTTAAC*GTC*C*C*

③ TC*C*TTTTC*C*C*C*GAC*AAC*C*TTTAC*

Fig. 4

LTR-EGFP Reportergen
Nicht aktivierte Kontrolle in HeLa
Excit.: 488 nm
Em.: 520 nm
Nukleus: DAPI Färbung
CLSM
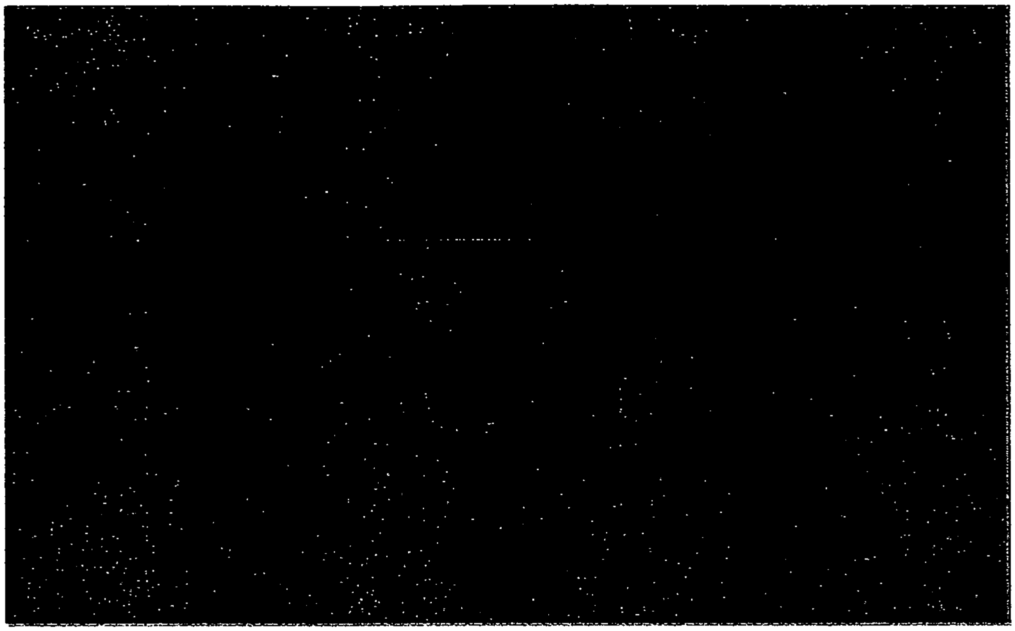
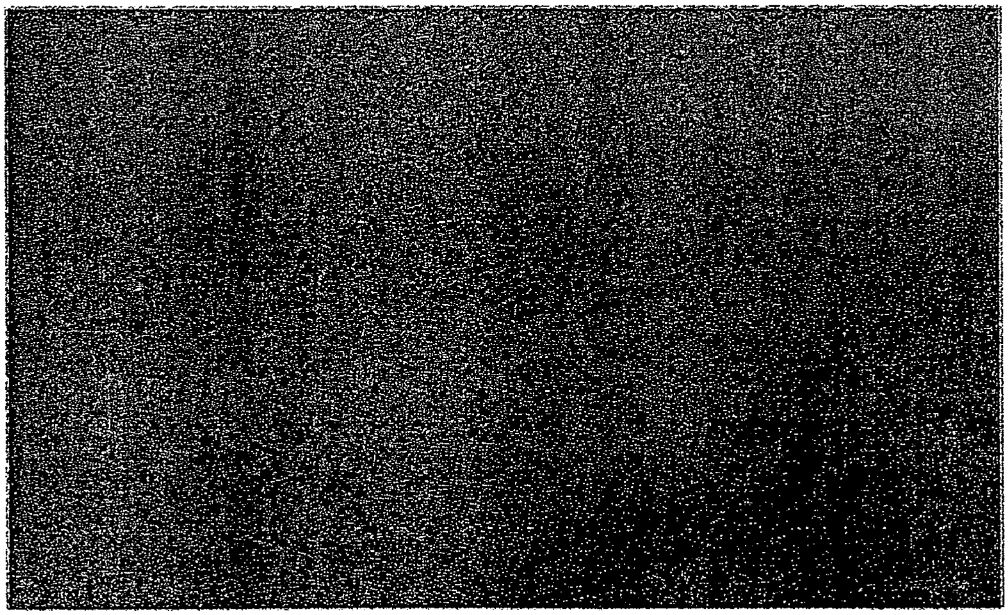
Fig. 5

LTR-EGFP Reportergen
Nach Aktivierung in HeLa
Excit.: 488 nm
Em.: 520 nm
Nukleus: DAPI Färbung
CLSM
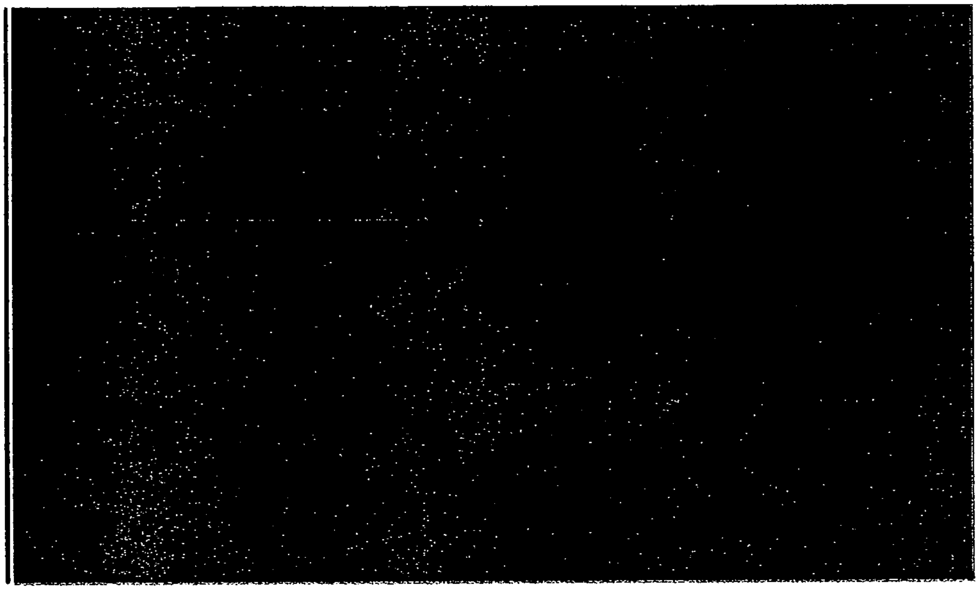
Fig. 6

PNA CONJUGATE FOR THE TREATMENT OF DISEASES ASSOCIATED WITH HIV

CROSS-REFERENCE TO RELATED APPLICATIONS

This application is filed under the provisions of 35 U.S.C. §371 and claims the priority of International Patent Application No. PCT/DE02/02564 filed Jul. 12, 2002, which in turn claims priority of German Patent Application No. 101 33 307.2 filed Jul. 12, 2001.

FIELD OF THE INVENTION

Background of the Invention

The present invention relates to peptide nucleic acid (PNA) conjugates which can be used for treating diseases correlated with HIV, the peptide nucleic acid (PNA) inhibiting the gene expression of HIV.

The incidence of the human immunodeficiency virus (HIV) is increasing world-wide in spite of the previous intensive research efforts made as to the development of effective treatment methods. HIV is counted among the lentiviral group of retroviruses and is one of the most intensively studied viruses. The HIV infection cycle starts with binding viral particles to the cell membrane of the target cells by means of a viral coat protein gp120/gp41. The virus initially binds to the CD4 protein, followed by binding to the obligatory co-receptor which is a member of the chemokin-receptor family. Main objectives of the HIV infection are T-helper cells and macrophages. Here, the viral core complex penetrates the cell and the virus is integrated into the viral genome in several steps (reverse transcription, introduction into the cell nucleus, integration into the chromosomes of the host cells as a DNA double strand). From this point of time, HIV is a permanent component of the cellular genome and can be considered an acquired genetic disease. HIV cannot replicate in the CD4+ cell and for the "priming" of its promoters in the regulatory region (LTR) it requires cellular transcription factor for the transcription of early regulatory mRNAs which code for Tat, Rev and Nef proteins. The transactivator protein Tat is of special significance in the early phase of HIV-RNA synthesis. The Tat protein concentration correlates directly with the HIV-RNA amount. The interaction between Tat and TAR can also result in a strongly increased trans-activation of the viral gene expression by inducing the initiation of transcription as well as elongation.

Previous therapy approaches which aimed at a causal treatment have not brought about a decisive breakthrough in combating infections. Drug therapies have not yet been able to either stop HIV infections or heal diseases caused by them. Immunological strategies, e.g. inoculations, have not yet been successful on account of the high variability of the expression patterns of the HIV virus coat proteins and it seems that they will not be very promising in the future either. Another theoretical therapy approach is based on a molecular virus inactivation, e.g. via antisense RNAs for blocking viral nucleic acids. Although this therapy approach offers itself particularly for HIV, it appears to be highly problematic on account of the transient control of the HIV infection cycle and the presently almost unknown viral expression pattern. It also seems that a HIV proliferation control by ribozymes is very difficult to realize because special suitable CUG sequences of the virus genome have to be identified for such a strategy (since the ribozymes only cleave at this sequence motif), which appears to be extremely difficult, above all with respect to the very high HIV mutation rate.

The problem of an effective introduction of the antisense or ribozyme molecules into the target location also arises in connection with all of the above discussed procedures. The vectors previously used for this purpose, e.g. adeno-associated viruses (AAVs) have numerous drawbacks. AAVs are small parvoviruses having a single-stranded DNA. Their potential is their ability of infecting both dividing and non-dividing cells and penetrating the host genome. However, their major drawback is the lack of synthesis of sufficient amounts and lack of stability as a vector for hematopoietic cells. Vectors based on MLV (murine leukemia virus) have also been tested in numerous clinical studies. Although they seem to be non-toxic and theoretically suited as possible carriers for antisense constructs, they have the drawback that only very low titers are achieved in the host. Finally, vectors based on LV (lentiviruses) might also come into consideration, however, their major drawback is that they can only infect non-proliferating cells. Although this property would permit the superinfection of HIV-infected cells, they are nevertheless unsuited on account of their natural viral tropism.

SUMMARY OF THE INVENTION

The present invention is thus based on the technical problem of providing products which permit a specific and efficient therapy based on an inhibition of the HIV gene expression.

This technical problem is solved by providing the embodiments characterized in the claims.

In order to obtain a solution to the technical problem, the inventors developed a conjugate comprising the following components:

- a transport mediator for the cell membrane ("P"),
- an address protein or peptide ("AP") for the import into the cell nucleus, and
- a peptide nucleic acid which is to be transported and can be hybridized with a HIV gene and inhibits the expression thereof ("PNA").

This modular conjugate has two decisive advantages:

(a) An efficient and site-directed PNA transport to the target location and thus a gene therapy is enabled by means of the components "P" and "AP". These components do not only permit a rapid and effective transport of macromolecules such as PNA through cell membranes of living cells into the cytoplasm but, following a cytoplasmic activation of address peptide sequences, also an efficient transport into the cell nucleus.

(b) The use of the protease-resistant and nuclease-resistant peptide nucleic acids (PNAs) which are oligonucleotide derivatives whose sugar phosphate backbone is preferably substituted by ethyl-amine-linked α-amino-ethyl-glycine units permits a stable and efficient blocking of the transcription of the desired gene under physiological conditions on account of their physicochemical properties. An anti-gene strategy based on the antisense principle is pursued by these PNAs. However, in this strategy, the target is not the mRNA but the gene itself, e.g. a viral DNA intermediate or the viral DNA integrated into the genomic host DNA. Here, the PNAs hybridize via the formation of a triple helix to the target DNA. The target region can be a transcribed region of the target DNA, on the one hand, or a regulatory region the blocking of which via the PNAs also inhibits the transcription, on the other hand.

Regarding methods as to the production of the individual components of the conjugates and their linkage reference is made to German patent application No. 199 33 492.7. The synthesis of PNAs is known to a person skilled in the art and also described in Nielsen et al., Science 254 (1991), 1497-1500, for example.

The structure of the conjugate according to the invention is preferably:

P - AP -(HIV-PNA)

more preferably with a spacer ("SP"):

P - AP - SP - (HIV-PNA)

The transport mediator for the cell membrane (abbreviated as "P" above) represents a peptide or protein which can pass through the plasma membrane. The length of this peptide or protein is not limited as long as it has the above property. Examples of "P" originate preferably from the penetratin family (Derossi et al., Trends Cell Biol. 8 (1988), pages 84-87) or are transportan or parts thereof (Pooga et al., The Faseb Journal 12 (1998), page 68 et seq.), those of the penetratin family being preferred. An example of "P" is a penetratin having the following sequence:

$NH_2$-RQIKIWFQNRRMKWKK-
(SEQ ID NO: 1)

The select "P" sequence is produced biologically (purification of natural transport mediator proteins or cloning and expression of the sequence in a eukaryotic or prokaryotic expression system) and preferably synthetically, e.g. according to the Merrifield method (Merrifield, J. Am. Chem. Soc. 85 (1963), 2149).

For the selection of the address protein peptide (abbreviated by "AP" above) the person skilled in the art can chose controlling peptides or polypeptides by means of the known amino acid sequences for the import into the cell nucleus. In principle, the length of this address peptide or protein is not limited as long as it has the property of ensuring a cell nucleus-specific transport. In general "APs", which contain a cell nucleus-specific recognition signal and thus direct the PNAs into the cell nucleus, are generally selected for the introduction of the PNAs. Fundamentally, the mere address sequence is sufficient for a transport into the cell nucleus. However, it is also possible to select "APs" which have a cell nucleus-specific peptidase cleavage site. Most favorably, this cleavage site is within the signal sequence but may also be attached thereto by additional amino acids to ensure the cleavage of the address sequence after reaching the cell nucleus. The select "AP" sequence is produced biologically (purification of natural transport mediator proteins or cloning and expression of the sequence in a eukaryotic or prokaryotic expression system) and preferably synthetically, e.g. according to the Merrifield method (Merrifield, J. Am. Chem. Soc. 85 (1963), 2149). Examples of suitable address proteins or peptides are:

-Pro-Pro-Lys-Lys-Lys-Arg-Lys-Val;
(SEQ ID NO: 2)
and $H_3N^+$-Pro-Lys-Lys-Lys-Arg-Lys-Val- -continued
(SEQ ID NO: 3)

(SEQ ID NO: 3 is a = nuclear localization sequence from SV40 T-antigen).

Furthermore, the conjugate can optionally contain a spacer (abbreviated by "SP" above) which is preferably located between the address protein/peptide and the peptide nucleic acid (PNA) to be transported. However, it may also be present additionally or alternatively between the transport mediator and the address protein. The spacer serves for eliminating or favorably influencing optionally existing steric interactions between the components. The spacer can be selected from e.g.: glycine, polylysine, polyethylene glycol (PEG), derivatives of polymethacrylic acid or polyvinyl pyrrolidone (PVP).

A redox cleavage site, e.g. -cysteine-S—S-cysteine-O—N—H, is preferably found between the transport mediator and the address protein/peptide. The bond forming between transport mediator and address protein is a redox coupling (mild cell-immanent linkage by means of DMSO; Rietsch and Beckwith, Annu. Rev. Genet. 32 (1998), 163-84):

Cysteine-SH SH-cysteine→cysteine-S—S-cystine

The peptide nucleic acid (PNA) permits the inhibition of the transcription of genes essential for HIV, e.g. in that it hybridizes with a gene region which is transcribed or a regulatory region, i.e. a region which is responsible for the activation of the expression of a certain gene or certain genes. Suitable genes and suitable regions can be identified by the person skilled in the art by means of the previously known HIV genes or the function thereof. The peptide nucleic acids preferably have a length of at least 18 bases, peptide nucleic acids with a length of at least 20 bases being particularly preferred. The peptide nucleic acid can also optionally be labeled, e.g. radioactively (e.g. linked with an alpha-, beta- or gamma radiator), with a dyestuff, with biotin/avidine, etc.

The conjugate constituents "P" and "AP" are synthesized preferably synthetically according to the Merrifield method (Merrifield, J. Am. Chem. Soc. 85 (1963), 2149). The other constituents (e.g. spacers and/or PNAs) are linked thereto by covalent chemical bond. The redox cleavage site is inserted between "P" and "AP" chemically by the above mentioned redox coupling. A covalent bond, preferably an acid amide bond, is also present between an optionally present spacer and the PNA or the address protein and the PNA. Possible alternatives are ether or ester bonds, depending on the functional group(s) existing in the substance to be conjugated.

In a particularly preferred embodiment of the conjugate according to the invention the peptide nucleic acid (PNA) hybridizes with the HIV-tat gene or HIV-rev gene. Based on the special viral HIV cycle the tat and rev genes are two preferred molecular targets for an anti-HIV therapy. The products of both genes act as essential regulatory proteins for trans-activating the HIV gene expression by binding to HIV-mRNA. Tat binds to TAR ("trans-activating-response-element") near the HIV-RNA 5' end and Rev interacts with RRE ("Rev-responsive-element") of the env gene.

The genomic organization of HIV-1 is shown in FIG. 1.

The sequences coding for HIV-1 are published in Ratner et al., Nature 313, pp. 277-284 (1985).

In a particularly preferred embodiment of the conjugate according to the invention, the PNAs hybridize with sequences of the HIV-1 LTR region (FIG. 2). Advantageous PNAs comprise the below sequences:

```
TTATTTCCTCTTTTGTTG
(SEQ ID NO: 4)

ATTAC*TAC*GTC*TC*TC*C*GTT
(SEQ ID NO: 5)

TATC*GGTTTTTAAC*GTC*C*C*
(SEQ ID NO: 6)

TC*C*TTTTC*C*C*C*GAC*AAC*C*TTTAC*
(SEQ ID NO: 7)
```

C* = is pseudoisocytosine

The use of pseudoisocytosine has the advantage that pH-independent hybridization is possible.

In another preferred embodiment, the PNAs are directed against the polypurine tract, central DNA flap, Nef or NCp7 (Vpr, Vpu [see FIG. 7]. For this purpose, the inventors conducted various experiments which are shown in FIGS. 9 to 13.

Preferred PNAs against the above-mentioned regions are as follows:

Sequences HIV-1 (Reference is made Herein to FIGS. 7-13)

Abbreviations:
L=linker
J=pseudoisocytosine or cytosine

```
For HIV:
c-PPT and 3'-PPT 4821-36/9116-31 (general sequence):          PNA I

(Polypurine tract)
N-TCC CCC CTT TTC TTT T-L-TTT TJT T
(SEQ ID NO: 8)

c-PPt target:
DNA (+) or RNA 4821-39
N-CA ATC CCC CCT TTT CTT T-L-TT TJT TT                         PNA Ia
(SEQ ID NO: 9)                                                 1) nbIaNLS+
                                                               2) nbIaNLS-

N-CA ATC CCC CCT TTT CTT T                                     PNA Ib
(SEQ ID NO: 10)                                                3) nbIbNLS+
(the same sequence without linker part)                        4) nbIbNLS-

DNA (-) 4800-20
N-GTA TTC ATC CAC AAT TTT                                      PNA II
(SEQ ID NO: 11)                                                5) nbIIaNLS+
                                                               6) nbIIbNLS-

DNA (+) 4800-20
N-AAA TTG TGG ATG AAT ACT                                      PNA III
(SEQ ID NO: 12)                                                7) nbIIIaNLS+
                                                               8) nbIIIbNLS-

Flap:                                                          PNA IV
DNA(-) 4861-80
N-TAG TAG ACA TAA TAG CAA                                      PNA IVa
(SEQ ID NO: 13)                                                9) nbIVaNLS-

Another DNA (-) between c-PPT and Tar to shorten the "flap" length:
DNA (+) 4841-60
N-TCC CCT GCA CTG TAC CCC                                      PNA IVb
(SEQ ID NO: 14)                                                10) nbVbNLS-

Nef:
DNA (-) 9095-9115
N-AGA TCT TAG CCA CTT TTT-C                                    PNA Va
(SEQ ID NO: 15)                                                11) nbVaNLS+

9136-56
N-GGC TAA TTC ACT CCC AAC-C                                    PNA Vb
(SEQ ID NO: 16)                                                12) nbVbNLS+

IN site (3') 9746-66:
N-TAG AGA TTT TCC ACA CTG                                      PNA Vc
(SEQ ID NO: 17)                                                13) nbVcNLS+

Seq is directed against the start of gag:
N-cac cca tct ctc tcc ttc (no linker)                          PNA VI
(SEQ ID NO: 18)                                                14) nbVINLS-

Splice acceptor site:
N-jtt jtt-L-ttc ttc ctg cca tag                                PNA VII
(SEQ ID NO: 55)                                                15) nbXNLS+
                                                               16) nbXNLS-

TAR:
N-cag gct caa atc tgg tct-L-tjt                                PNA VII
(SEQ ID NO: 19)                                                17) nbXNLS-
```

-continued

```
NCp7:
N-ATT ACT ACG TCT CTC CGT (not tested)            PNA VIII
(SEQ ID NO: 20)
N-TAT CGG TTT TTA ACG TCC                         18) smVIIIaNLS+
(SEQ ID NO: 21)
N T TTT JJT-linker-TCC TTT TCC CCG ACA ACC        19) smVIIIaNLS+
(SEQ ID NO: 22)                                   20) smVIIIcNLS+

Random sequence as a control:
N-CAT ACT TGA CTC GTT ATC-C                       PNA IX
(SEQ ID NO: 23)
N-CAT ACT TGA CTC GTT ATC-C                       21) IX NLS-
(SEQ ID NO: 24)                                   22) IX NLS+

BDV PNA: (This sequence was tested for BDV spreading; FIG. 8)
N-TCC CTA CGC CGC CTT CTC-C terminus
(SEQ ID NO: 25)
```

In another preferred embodiment the PNAs (e.g. PNA VI above) are directed against the viral RNA, the molecular target representing the Gag-splice acceptor site.

Finally, the present invention also relates to a medicament containing a conjugate according to the invention, optionally together with a suitable carrier, and to the use thereof for an HIV therapy. In this connection, in particular the parenteral or intravenous application has proved suited.

The invention is further described by means of the figures wherein:

FIG. 2 shows sequences of the HIV-1LTR region

FIG. 4 shows viral sites of attack of the pseudo-isocytosine-containing PNAs FIG. 5 shows CLSM pictures (non-activated control in HeLa)

FIG. 6 shows CLSM pictures (after activation in HeLa)

The invention is further described by means of the below examples.

EXAMPLE 1

The HIV-1 "long terminal repeat" (LTR) codes for the transcription promoter. Sequence analyses prove the existence of a single LTR enhancer promoter configuration for all of the presently studied HIV-1 subtypes. Transcription studies using EGF reporter constructs show its functionality.

LTR-EGF construct:

Based on biocomputing data, the sequence AC S72615, which relates to the HIV subtype HIV4B6 was selected representatively using the HUSAR program of DKFZ, the SRS (sequence Retrieval System) and the multiple alignment algorithm (MALIGN) (Shiramizu et al., Cancer Res. 65, pp. 2069-2072 (1994)).

HIV4B6-LTR:

CCAATAAAGG AGAAAACAAC TGCTTGTTAC

ACCC$_{(-18)}$TATAAG CCAGCATAAA GC$_{(+1)}$ATG GA (SEQ ID NO: 26)

Figure 1:
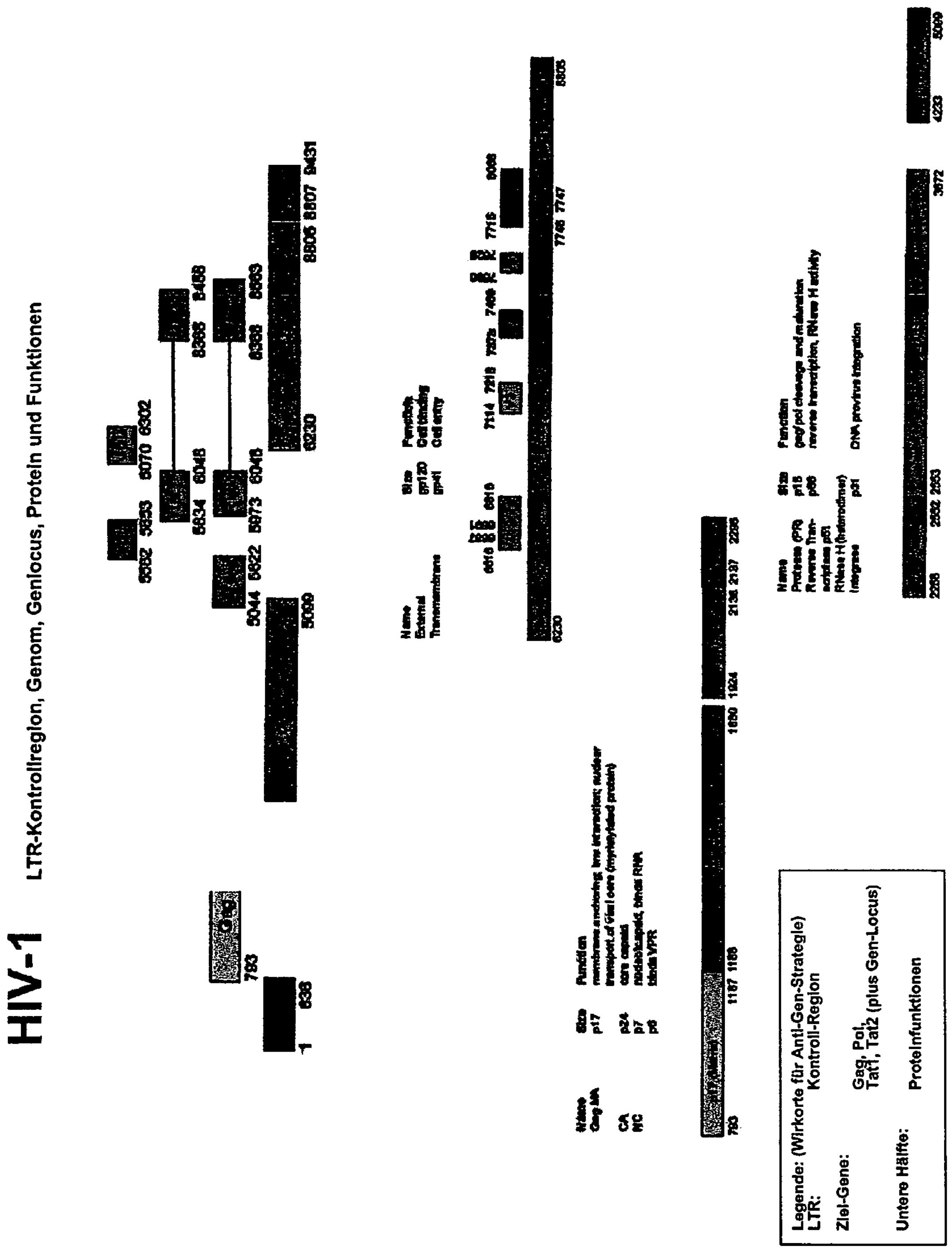
FIG. 1 shows the genomic organization of HIV-1
Figure 3:
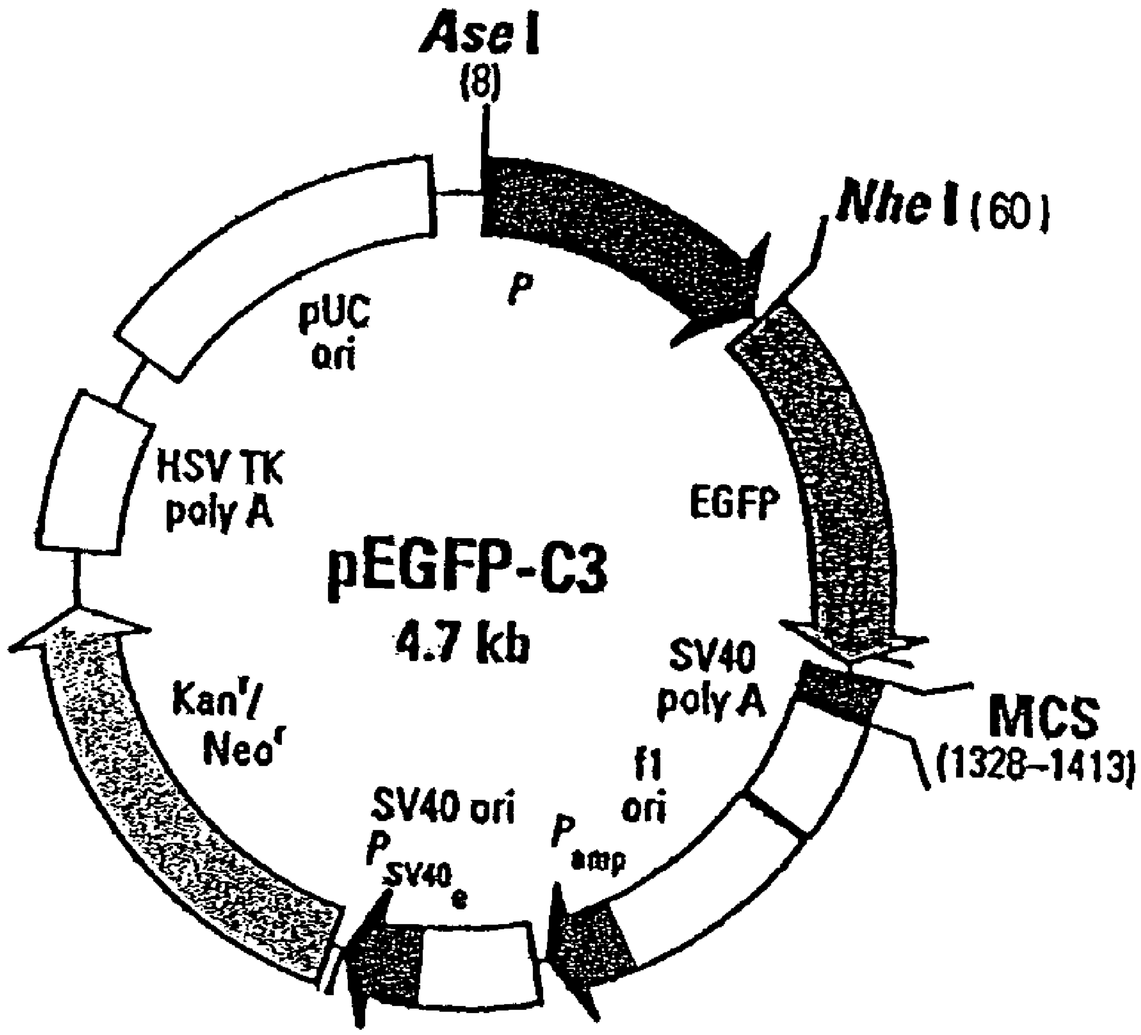
FIG. 3 shows a plasmid map of pEGFP-C3
Figure 7:
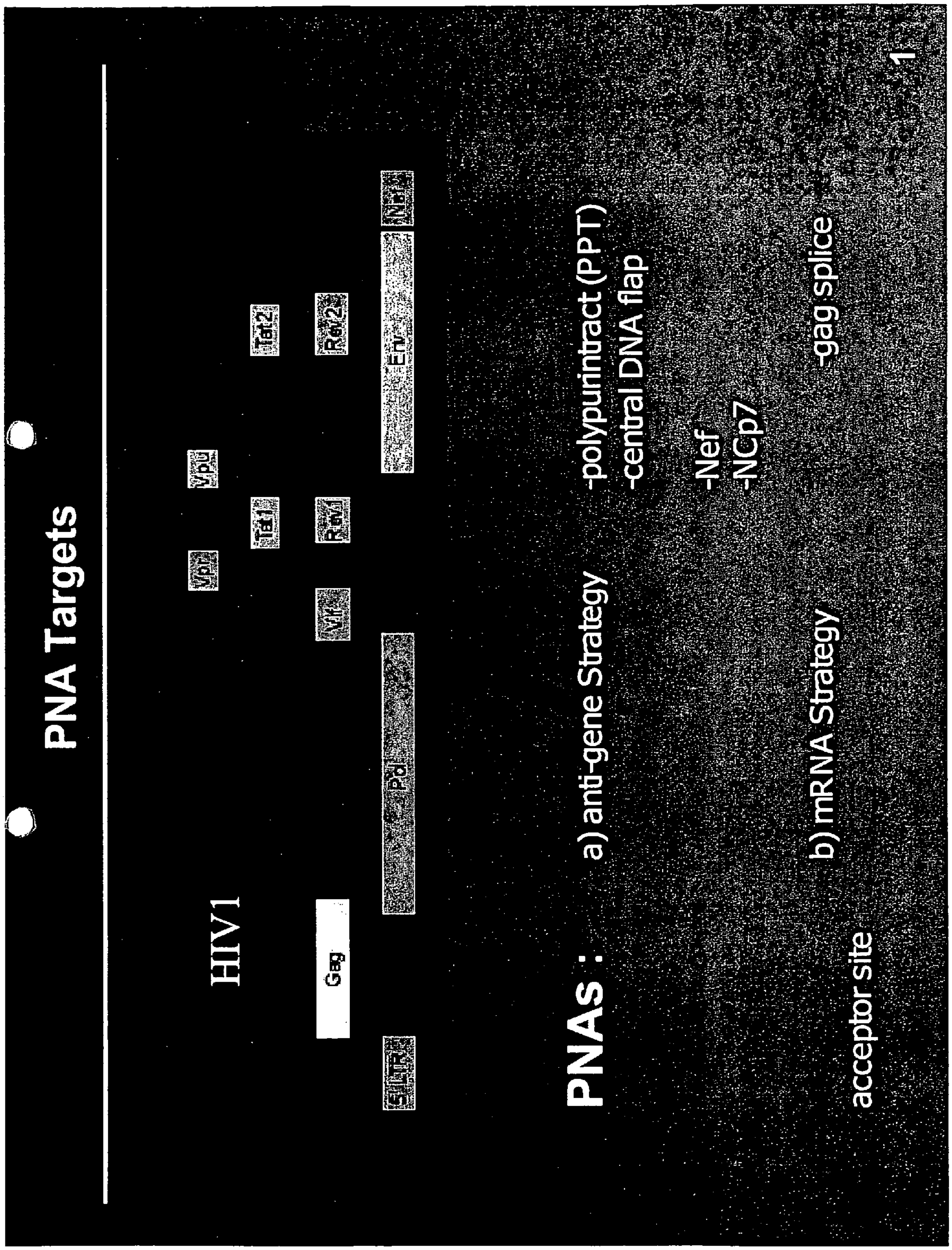
FIG. 7 shows PNA targets
Figure 8:
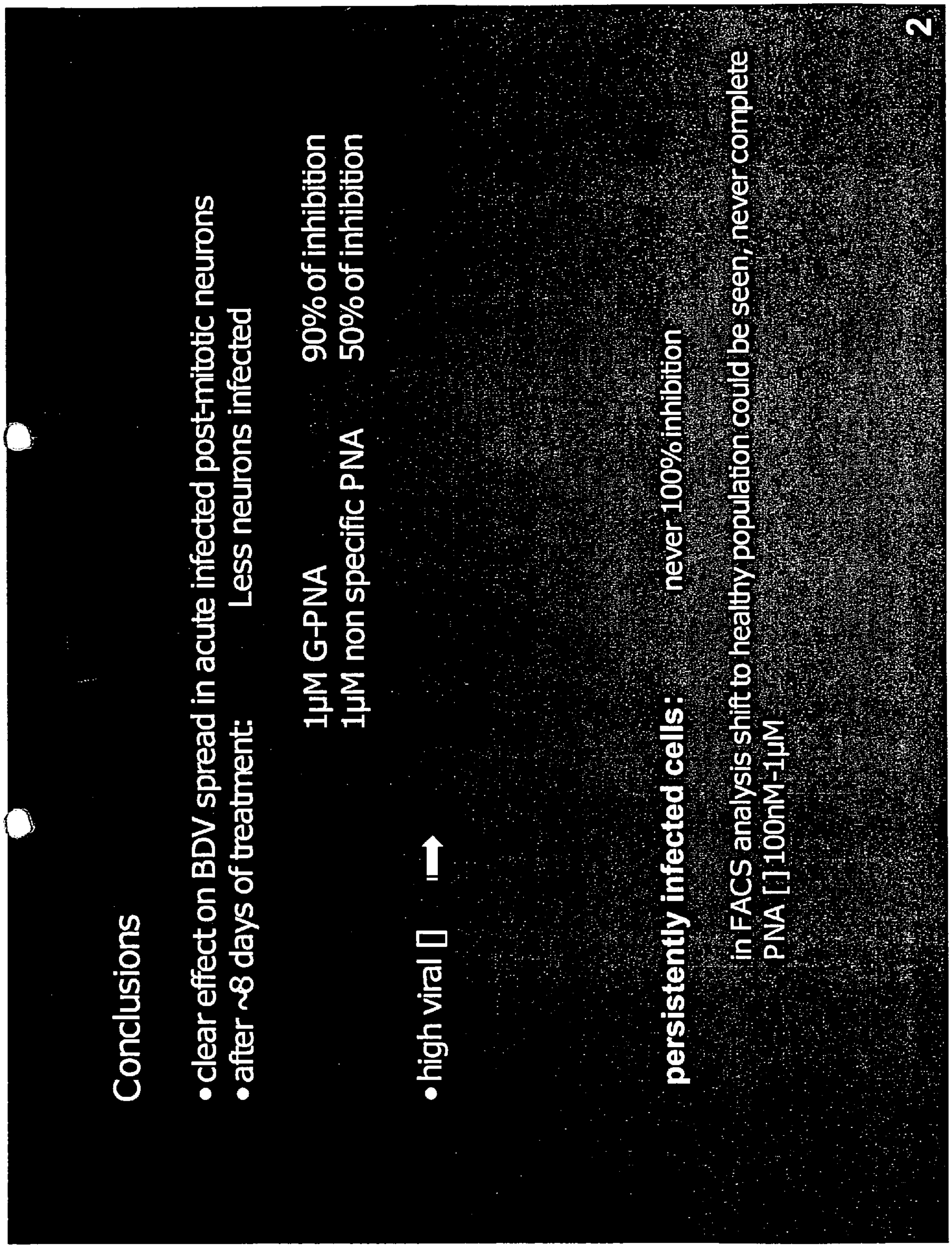
FIG. 8 shows studies of BDV (Borna disease virus; retrovirus) instead of HIV to prove that other retroviruses can also be inhibited by PNA constructs

The Ase I (8/−52)-Nhe I (64/+1)-LTR fragment was synthesized according to the known phosphoramidite method and cloned into a pEGFP-C3/Variant (without PCMV) (FIG. 3) (Clontech company, Heidelberg).

Cloned Fragment:

3′-$_{(-52)}$CCAATAAAGG AGAAAACAACTGCCTTGTTAC ACCC$_{(-18)}$TATAAGCCAGCATAAA GC-5′ (SEQ ID NO: 27)

Then, the plasmid DNA was replicated in *E. coli* in LB-Amp culture medium under ampicillin selection pressure. The isolation and preparation of the plasmid DNA were carried out with the Mini-Prep-DNA kit (Clontech company) according to the manufacturer's instructions.

Cell culture and transfection assay:

The human cervical carcinoma suspension cell line HeLa-S (tumor bank DKFZ) was used. The cells were cultured in MEM"Joklik" (Minimal Essential Medium; Sigma company) with 10% FCS (Sigma company), glutamine (Gibco company) in a $CO_2$ atmosphere at 37° C.

The following shuttle construct was produced:

RQIKIWFQNRRMKWKK-SS-PKKKEKV-GG-GK-TTA TTT CCT CTT TTG TTG (SEQ ID NO: 28)
→ TTA TTT CCT (= for stabilization) (SEQ ID NO: 29)

This construct was transfected into the HeLa cells according to the Britten and Kohne protocol (Science, Vol. 161, No. 3841, pp. 529-540, 1986). HeLa-S is transfected by direct addition of the shuttle construct to the culture medium at a concentration of 100 pM at 37° C. for 3 hours under incubation in 5% $CO_2$ atmosphere. Then, the hybridization was carried out with the LTR-EGF construct analogously to the above mentioned Britten and Kohne protocol. The following complex forms:

GG-GK-TTA TTT CCT CTT TTG TTG (SEQ ID NO: 28)
AAT AAA GGA GAA AAC AAC (SEQ ID NO: 56)
→ TTA TTT CCT (SEQ ID NO: 29)

The HeLa-S cells are cultured in 8-chamber glass plates in Petri dishes under 5% $CO_2$ at 370 for 48 hours.

In order to activate the plasmid, it is necessary to separate the shuttle system from the plasmid DNA. For this purpose, the plates are heated to 45° C. in a water bath for 1 minute. Having changed the medium, the HeLa-S cells are further cultured. The transcription determination of GFP under LTR control is effected by means of fluorescence reader analysis after 48, 72 and 96 hours (excitation: 488 nm; emission: 520 nm). GFP is localized by means of confocal laser scanning microscopy (CLSM) analogously but in 8-chamber glass plates in Petri dishes under 5% $CO_2$ at 37° C. for 48, 72 and 96 hours (excitation: 488 nm; emission: 520 nm). The results are shown in FIGS. 5 and 6.

EXAMPLE 2

Figure 9:
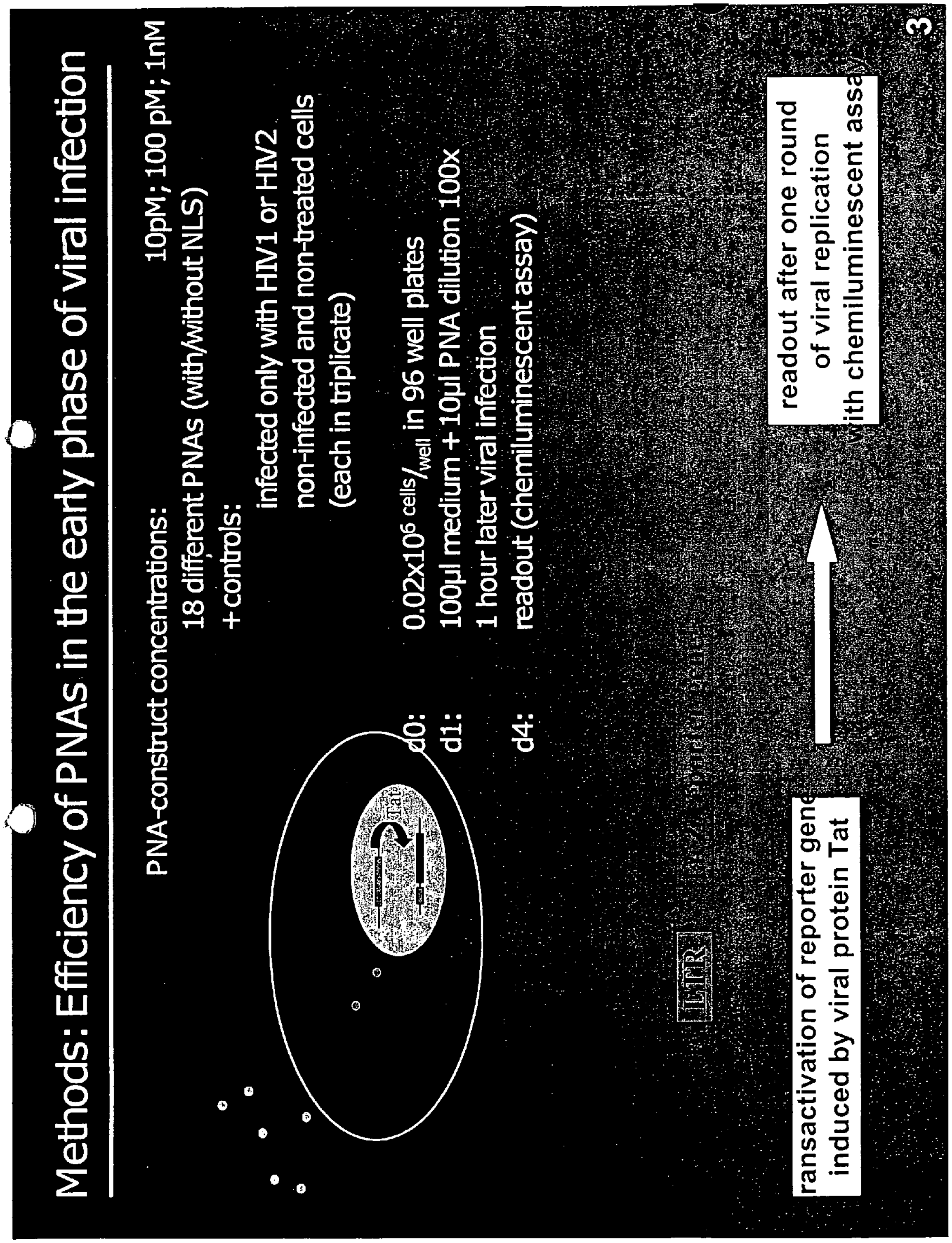
FIG. 9 shows the efficiency of PNA in the early phase of viral infection The biological effect was measured by transactivation of a reporter gene construct (LacZ)
Figure 10:
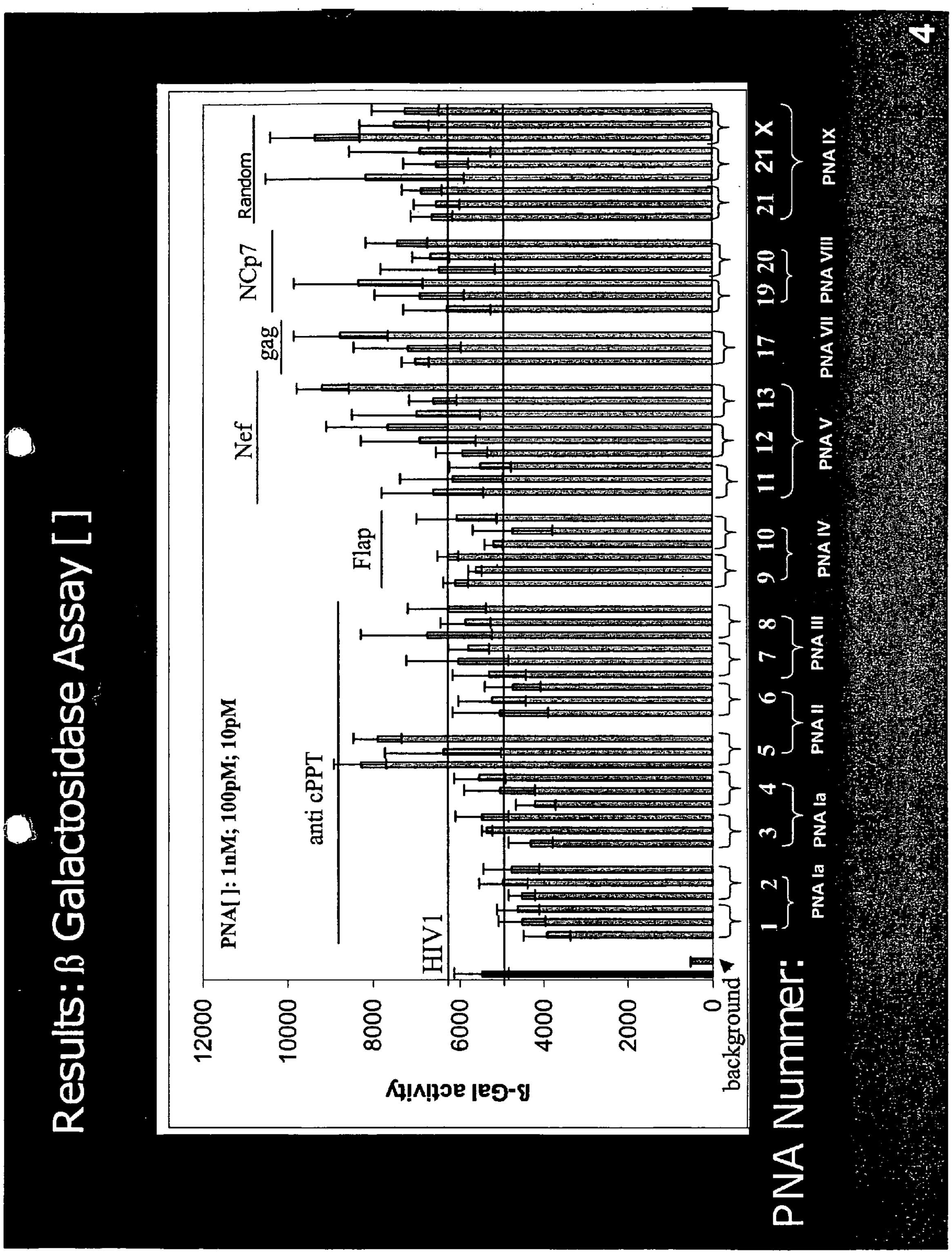
FIG. 10 shows the results of the reporter gene assay after treatment with different PNAs. Significant results were observed with PNAs against cPPT (polypurine tract)
Figure 11:
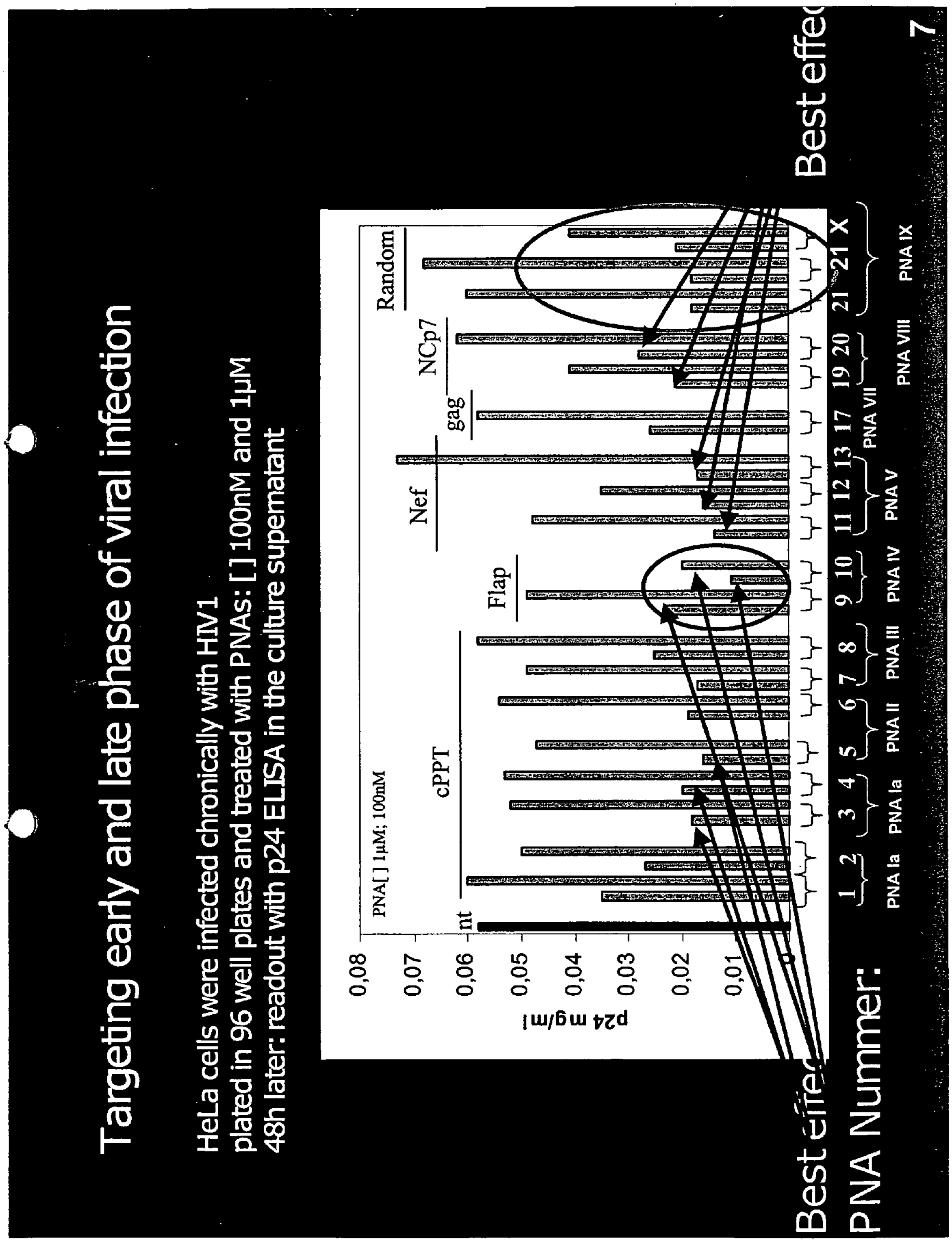
FIG. 11 shows the use of PNAs in the early and late phases of viral infection; testing by ELISA against p24 virus protein. Different PNAs against cPPT/flap/Nef/gag/random were capable of drastically reducing the viral p24
Figure 12:
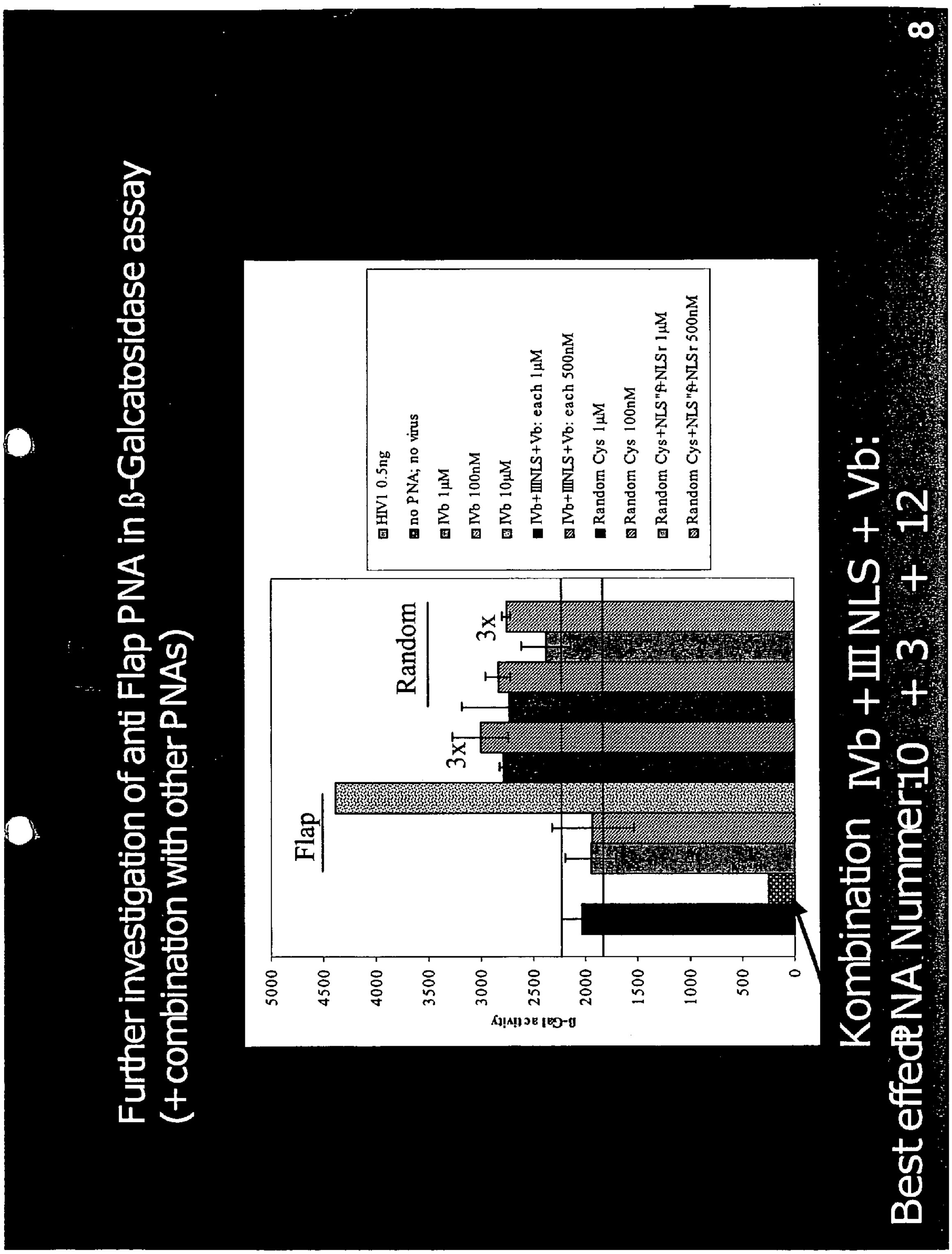
FIG. 12 shows the reporter gene assay with anti-FLAP PNA combined with other PNAs. The combination of PNA [IVb]+PNA[IIINLS]+PNA[Vb] (500 nM concentration) resulted in an optimum β-Gal reduction.
Figure 13:
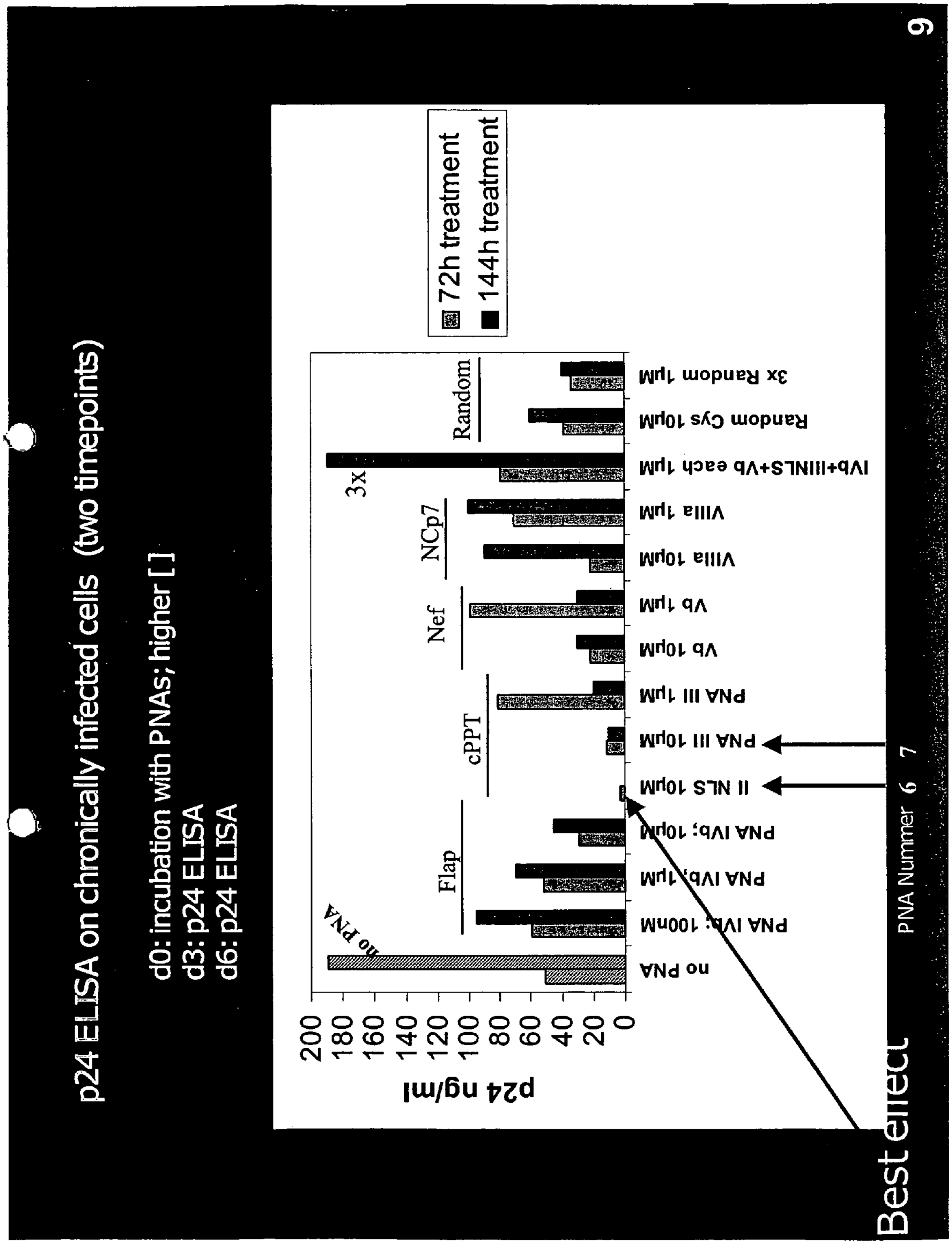
FIG. 13 shows that chronically HIV-infected cells were studied by viral p24 ELISA following PNA treatment (72 and 144 h after the PNA application). The best effect was obtained with cPPT (polypurine tract) by PNA[IINLS].

Here, a method is described which permits to determine a PNA effect in an early infection phase of HIV-1. Reference is made to FIGS. 9-11.

HeLa cells which were transfected with a stably expressed LacZ reporter gene were used as a model. The test was carried out in a 96-well plate. HeLa cells are suspended in RPMI medium and plated out. The cell number was 20000 cells per well. The pipetting volume is 100 µl/well. 18 different PNA sequences (see FIG. 10) plus one control were tested (X=further viral control (e.g. BDV)). The PNA construct concentrations were 10 pM, 100 pM and 1 nM. The PNA constructs were produced in analogy with Example 1. After one hour, the viral infection was effected. The viral effect on the LTR promoter was determined via LacZ activity by means of a photometer.

The invention claimed is:

1. A conjugate for mediating a cell nucleus-specific transport of a peptide nucleic acid (PNA) which hybridizes to DNA of HIV and inhibits the transcription of the DNA of a transcribable HIV gene or a HIV gene involved in the regulation of gene expression or a part thereof, wherein the conjugate comprises the following components:

a) a transport peptide or protein which can pass through the plasma cell membrane, b) an address protein or peptide for the import into the cell nucleus which contains a nucleus-recognition signal, and c) a peptide nucleic acid (PNA) comprising a sequence selected from SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 21, SEQ ID NO: 22, TTATTTCCTCTTTTGTTG (SEQ ID NO: 4), ATTAC*TAC*GTC*TC*TC*C*GTT (SEQ ID NO: 5), TATC *GGTTTTTAAC*GTC*C*C* (SEQ ID NO: 6), and, TC*C*TTTTC*C*C*C*GAC*AAC*C*TTTAC* (SEQ ID NO: 7), wherein C* is pseudoisocytosine, wherein the PNA is to be transported and hybridizes to DNA of HIV and inhibits the transcription thereof, wherein said DNA is selected from the group consisting of polypurine tract, central DNA flap, Nef, NCp7 and LTR region.

2. The conjugate according to claim 1 wherein the transport protein or peptide has the following sequence: $NH_2$-RQIKIWFQNRRMKWKK-(SEQ ID NO: 1) and wherein the address protein or peptide is selected from:

Pro-Pro-Lys-Lys-Lys-Arg-Lys-Val; and
(SEQ ID NO: 2)

$H_3N^+$-Pro-Lys-Lys-Lys-Arg-Lys-Val,
(SEQ ID NO: 3)

wherein SEQ ID NO: 3 is the nuclear localization sequence from SV40-T antigen.

3. The conjugate according to claim 1, wherein the conjugate has the following structure:

transport peptide or protein-address protein-peptide nucleic acid (PNA).

4. The conjugate according to claim 1, wherein the peptide nucleic acid is protease-resistant and nuclease-resistant.

5. The conjugate according to claim 1, wherein the peptide nucleic acid has a sugar phosphate backbone substituted by ethyl-amine-linked α-amino-ethyl-glycine units.

6. The conjugate according to claim 1, wherein a redox-cleavage site is between the transport protein/peptide and the address peptide.

7. The conjugate according to claim 1, wherein the PNA has a length of at least 18 bases.

* * * * *

SEQUENCE LISTING

```
<160> NUMBER OF SEQ ID NOS: 54

<210> SEQ ID NO 1
<211> LENGTH: 16
<212> TYPE: PRT
<213> ORGANISM: Homo sapiens

<400> SEQUENCE: 1

Arg Gln Ile Lys Ile Trp Phe Gln Asn Arg Arg Met Lys Trp Lys Lys
1               5                   10                  15


<210> SEQ ID NO 2
<211> LENGTH: 8
<212> TYPE: PRT
<213> ORGANISM: Artificial Sequence
<220> FEATURE:
<223> OTHER INFORMATION: Addressprotein

<400> SEQUENCE: 2

Pro Pro Lys Lys Lys Arg Lys Val
1               5


<210> SEQ ID NO 3
<211> LENGTH: 7
<212> TYPE: PRT
<213> ORGANISM: Artificial Sequence
<220> FEATURE:
<223> OTHER INFORMATION: Addressprotein

<400> SEQUENCE: 3

Pro Lys Lys Lys Arg Lys Val
1               5
```

-continued

<210> SEQ ID NO 4
<211> LENGTH: 18
<212> TYPE: DNA
<213> ORGANISM: Artificial Sequence
<220> FEATURE:
<223> OTHER INFORMATION: PNA

<400> SEQUENCE: 4
ttatttcctc ttttgttg 18

<210> SEQ ID NO 5
<211> LENGTH: 19
<212> TYPE: DNA
<213> ORGANISM: Artificial Sequence
<220> FEATURE:
<223> OTHER INFORMATION: PNA

<400> SEQUENCE: 5
attactacgt ctctccgtt 19

<210> SEQ ID NO 6
<211> LENGTH: 19
<212> TYPE: DNA
<213> ORGANISM: Artificial Sequence
<220> FEATURE:
<223> OTHER INFORMATION: PNA

<400> SEQUENCE: 6
tatcggtttt taacgtccc 19

<210> SEQ ID NO 7
<211> LENGTH: 23
<212> TYPE: DNA
<213> ORGANISM: Artificial Sequence
<220> FEATURE:
<223> OTHER INFORMATION: PNA

<400> SEQUENCE: 7
tccttttccc cgacaacctt tac 23

<210> SEQ ID NO 8
<211> LENGTH: 23
<212> TYPE: DNA
<213> ORGANISM: Artificial Sequence
<220> FEATURE:
<223> OTHER INFORMATION: PNA I

<400> SEQUENCE: 8
tccccccttt tcttttttt ctt 23

<210> SEQ ID NO 9
<211> LENGTH: 25
<212> TYPE: DNA
<213> ORGANISM: Artificial Sequence
<220> FEATURE:
<223> OTHER INFORMATION: PNA Ia

<400> SEQUENCE: 9
caatcccccc ttttcttttt tcttt 25

<210> SEQ ID NO 10
<211> LENGTH: 18
<212> TYPE: DNA
<213> ORGANISM: Artificial Sequence
<220> FEATURE:
<223> OTHER INFORMATION: PNA Ib -continued

<400> SEQUENCE: 10
caatcccccc ttttcttt 18

<210> SEQ ID NO 11
<211> LENGTH: 18
<212> TYPE: DNA
<213> ORGANISM: Artificial Sequence
<220> FEATURE:
<223> OTHER INFORMATION: PNA II

<400> SEQUENCE: 11
gtattcatcc acaatttt 18

<210> SEQ ID NO 12
<211> LENGTH: 18
<212> TYPE: DNA
<213> ORGANISM: Artificial Sequence
<220> FEATURE:
<223> OTHER INFORMATION: PNA III

<400> SEQUENCE: 12
aaattgtgga tgaatact 18

<210> SEQ ID NO 13
<211> LENGTH: 18
<212> TYPE: DNA
<213> ORGANISM: Artificial Sequence
<220> FEATURE:
<223> OTHER INFORMATION: PNA IV

<400> SEQUENCE: 13
tagtagacat aatagcaa 18

<210> SEQ ID NO 14
<211> LENGTH: 18
<212> TYPE: DNA
<213> ORGANISM: Artificial Sequence
<220> FEATURE:
<223> OTHER INFORMATION: PNA IVb

<400> SEQUENCE: 14
tcccctgcac tgtacccc 18

<210> SEQ ID NO 15
<211> LENGTH: 18
<212> TYPE: DNA
<213> ORGANISM: Artificial Sequence
<220> FEATURE:
<223> OTHER INFORMATION: PNA Va

<400> SEQUENCE: 15
agatcttagc cacttttt 18

<210> SEQ ID NO 16
<211> LENGTH: 18
<212> TYPE: DNA
<213> ORGANISM: Artificial Sequence
<220> FEATURE:
<223> OTHER INFORMATION: PNA Vb

<400> SEQUENCE: 16
ggctaattca ctcccaac 18

<210> SEQ ID NO 17

-continued

<211> LENGTH: 18
<212> TYPE: DNA
<213> ORGANISM: Artificial Sequence
<220> FEATURE:
<223> OTHER INFORMATION: PNA Vc

<400> SEQUENCE: 17
tagagatttt ccacactg 18

<210> SEQ ID NO 18
<211> LENGTH: 18
<212> TYPE: DNA
<213> ORGANISM: Artificial Sequence
<220> FEATURE:
<223> OTHER INFORMATION: PNA VI

<400> SEQUENCE: 18
cacccatctc tctccttc 18

<210> SEQ ID NO 19
<211> LENGTH: 21
<212> TYPE: DNA
<213> ORGANISM: Artificial Sequence
<220> FEATURE:
<223> OTHER INFORMATION: PNA VII

<400> SEQUENCE: 19
caggctcaaa tctggtcttc t 21

<210> SEQ ID NO 20
<211> LENGTH: 18
<212> TYPE: DNA
<213> ORGANISM: Artificial Sequence
<220> FEATURE:
<223> OTHER INFORMATION: PNA VIII

<400> SEQUENCE: 20
attactacgt ctctccgt 18

<210> SEQ ID NO 21
<211> LENGTH: 18
<212> TYPE: DNA
<213> ORGANISM: Artificial Sequence
<220> FEATURE:
<223> OTHER INFORMATION: PNA VIII

<400> SEQUENCE: 21
tatcggtttt taacgtcc 18

<210> SEQ ID NO 22
<211> LENGTH: 25
<212> TYPE: DNA
<213> ORGANISM: Artificial Sequence
<220> FEATURE:
<223> OTHER INFORMATION: PNA VIII

<400> SEQUENCE: 22
ttttccttcc ttttccccga caacc 25

<210> SEQ ID NO 23
<211> LENGTH: 18
<212> TYPE: DNA
<213> ORGANISM: Artificial Sequence
<220> FEATURE:
<223> OTHER INFORMATION: PNA IX

<400> SEQUENCE: 23

-continued catacttgac tcgttatc 18

<210> SEQ ID NO 24
<211> LENGTH: 18
<212> TYPE: DNA
<213> ORGANISM: Artificial Sequence
<220> FEATURE:
<223> OTHER INFORMATION: PNA IX

<400> SEQUENCE: 24
catacttgac tcgttatc 18

<210> SEQ ID NO 25
<211> LENGTH: 18
<212> TYPE: DNA
<213> ORGANISM: Artificial Sequence
<220> FEATURE:
<223> OTHER INFORMATION: BDV PNA

<400> SEQUENCE: 25
tccctacgcc gccttctc 18

<210> SEQ ID NO 26
<211> LENGTH: 57
<212> TYPE: DNA
<213> ORGANISM: Human immunodeficiency virus

<400> SEQUENCE: 26
ccaataaagg agaaaacaac tgcttgttac accctataag ccagcataaa gcatgga 57

<210> SEQ ID NO 27
<211> LENGTH: 53
<212> TYPE: DNA
<213> ORGANISM: Artificial Sequence
<220> FEATURE:
<223> OTHER INFORMATION: Cloned fragment

<400> SEQUENCE: 27
ccaataaagg agaaaacaac tgccttgtta caccctataa gccagcataa agc 53

<210> SEQ ID NO 28
<211> LENGTH: 18
<212> TYPE: DNA
<213> ORGANISM: Artificial Sequence
<220> FEATURE:
<223> OTHER INFORMATION: Shuttle-construct

<400> SEQUENCE: 28
ttatttcctc ctttgttg 18

<210> SEQ ID NO 29
<211> LENGTH: 9
<212> TYPE: DNA
<213> ORGANISM: Artificial Sequence
<220> FEATURE:
<223> OTHER INFORMATION: Shuttle-construct

<400> SEQUENCE: 29 ttatttcct 9

<210> SEQ ID NO 30
<211> LENGTH: 2460
<212> TYPE: DNA
<213> ORGANISM: Human immunodeficiency virus -continued

<400> SEQUENCE: 30

```
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180
acaaaggaga gaacaccagc ttgttacacc ctgtgagcct gcatggaatg gatgacccgg     240
agagagaagt gttagagtgg aggtttgaca gccgcctagc atttcatcac atggcccgag     300
agctgcatcc ggagtacttc aagaactgct gacatcgagc ttgctacaag ggactttccg     360
ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata aagcttgcct     540
tgagtgcttc aagtagtgtg tgcccgtctg ttgtgtgact ctggtaacta gagatccctc     600
agaccctttt agtcagtgtg gaaaatctct agcagtggcg cccgaacagg gacctgaaag     660
cgaaagggaa accagaggag ctctctcgac gcaggactcg gcttgctgaa gcgcgcacgg     720
caagaggcga ggggcggcga ctggtgagta cgccaaaaat tttgactagc ggaggctaga     780
aggagagaga tgggtgcgag agcgtcagta ttaagcgggg gagaattaga tcgatgggaa     840
aaaattcggt taaggccagg gggaaagaaa aaatataaat taaaacatat agtatgggca     900
agcagggagc tagaacgatt cgcagttaat cctggcctgt tagaaacatc agaaggctgt     960
agacaaatac tgggacagct acaaccatcc cttcagacag gatcagaaga acttagatca    1020
ttatataata cagtagcaac cctctattgt gtgcatcaaa ggatagagat aaaagacacc    1080
aaggaagctt tagacaagat agaggaagag caaaacaaaa gtaagaaaaa agcacagcaa    1140
gcagcagctg acacaggaca cagcaatcag gtcagccaaa attaccctat agtgcagaac    1200
atccaggggc aaatggtaca tcaggccata tcacctagaa ctttaaatgc atgggtaaaa    1260
gtagtagaag agaaggcttt cagcccagaa gtgataccca tgttttcagc attatcagaa    1320
ggagccaccc cacaagattt aaacaccatg ctaaacacag tggggggaca tcaagcagcc    1380
atgcaaatgt taaaagagac catcaatgag gaagctgcag aatgggatag agtgcatcca    1440
gtgcatgcag ggcctattgc accaggccag atgagagaac caaggggaag tgacatagca    1500
ggaactacta gtacccttca ggaacaaata ggatggatga caaataatcc acctatccca    1560
gtaggagaaa tttataaaag atggataatc ctgggattaa ataaaatagt aagaatgtat    1620
agccctacca gcattctgga cataagacaa ggaccaaagg aaccctttag agactatgta    1680
gaccggttct ataaaactct aagagccgag caagcttcac aggaggtaaa aaattggatg    1740
acagaaacct tgttggtcca aaatgcgaac ccagattgta agactatttt aaaagcattg    1800
ggaccagcgg ctacactaga agaaatgatg acagcatgtc agggagtagg aggacccggc    1860
cataaggcaa gagttttggc tgaagcaatg agccaagtaa caaattcagc taccataatg    1920
atgcagagag gcaattttag gaaccaaaga aagattgtta agtgtttcaa ttgtggcaaa    1980
gaagggcaca cagccagaaa ttgcagggcc cctaggaaaa agggctgttg gaaatgtgga    2040
aaggaaggac accaaatgaa agattgtact gagagacagg ctaatttttt agggaagatc    2100
tggccttcct acaagggaag gccagggaat tttcttcaga gcagaccaga gccaacagcc    2160
ccaccagaag agagcttcag gtctggggta gagacaacaa ctccccctca gaagcaggag    2220
ccgatagaca aggaactgta tcctttaact tccctcaggt cactctttgg caacgacccc    2280
tcgtcacaat aaagataggg ggcaactaa aggaagctct attagataca ggagcagatg    2340
```

-continued atacagtatt agaagaaatg agtttgccag gaagatggaa accaaaaatg atagggggaa 2400
ttggaggttt tatcaaagta agacagtatg atcagatact catagaaatc tgtggacata 2460

<210> SEQ ID NO 31
<211> LENGTH: 181
<212> TYPE: DNA
<213> ORGANISM: Human immunodeficiency virus
<220> FEATURE:
<221> NAME/KEY: misc_feature
<222> LOCATION: (123)..(123)
<223> OTHER INFORMATION: n is a, c, g, or t

<400> SEQUENCE: 31
gcctggccat aaagcaagaa ttttggctga ggcaatgagc caggtaacaa atacrgctgt 60
aatgatgcag cgaaacaact ttaagggtca aagaaaaatt attaaatgtt tcaactgtgg 120
canggaggga cytagcaaaa aattgcaggg cccctaggdd gddgggttgt tggaaatgta 180
a 181

<210> SEQ ID NO 32
<211> LENGTH: 213
<212> TYPE: DNA
<213> ORGANISM: Human immunodeficiency virus

<400> SEQUENCE: 32
catgtcgggg agtgggagga cctagccaca aagccagagt gttggctgag gcaatgagcc 60
aagcaaataa tacaaacata atgatgcaga gaaacaactt taaaggccct aaaagaatta 120
ttaaatgttt caactgtggc aaggaagggc acttagccag aaattgcagg gcccctagga 180
aaaaaggctg ttggaaatgt ggaaaggaag gac 213

<210> SEQ ID NO 33
<211> LENGTH: 202
<212> TYPE: DNA
<213> ORGANISM: Human immunodeficiency virus
<220> FEATURE:
<221> NAME/KEY: misc_feature
<222> LOCATION: (140)..(142)
<223> OTHER INFORMATION: n is a, c, g, or t

<400> SEQUENCE: 33
catgtcasgg agtgggggac ccggccataa agcaagagtt ttggctgaag caatgagcca 60
agtaacacca ccagctaaca taatgatgca gagaggcaat tttaggaacc aaagaaagac 120
tgttaagtgt ttcaattgtn nndaagaagg gcayatagcc aaaaattgca gggcccctag 180
gaadaagggc tgttggaaat gt 202

<210> SEQ ID NO 34
<211> LENGTH: 192
<212> TYPE: DNA
<213> ORGANISM: Human immunodeficiency virus
<220> FEATURE:
<221> NAME/KEY: misc_feature
<222> LOCATION: (6)..(6)
<223> OTHER INFORMATION: n is a, c, g, or t

<400> SEQUENCE: 34
cataangcaa gagttttggc tgaagcaatg agccaagtaa cacaaccagc taccataatg 60
atgcagagag gcaattttag gaaccaaaga aagactgtta agtgtttcaa ttgbbbvaaa 120
gaagggcaca tagccaaaaa ttgcagggcc cctaggaaaa agggctgttg gaaatgtggt 180

-continued

```
agggaaggac ac                                                192

<210> SEQ ID NO 35
<211> LENGTH: 206
<212> TYPE: DNA
<213> ORGANISM: Human immunodeficiency virus

<400> SEQUENCE: 35

agtgggaggm cccggccama aagcaagggt tttggcggaa gcaatgagcc aagtaacaaa     60

ttcacctgcc ataatgatgc agagaggcaa ttttaggaac caaagaaaaa ctgttaagtg    120

tttcaattgt ggcaaagaag ggcacatagc caaaaattgc agggccccta ggaaaagggg    180

ctgttggaaa tgtgghaagg aaggam                                         206

<210> SEQ ID NO 36
<211> LENGTH: 206
<212> TYPE: DNA
<213> ORGANISM: Human immunodeficiency virus

<400> SEQUENCE: 36

agtgggaggm cccggccama aagcaagggt tttggcggaa gcaatgagcc aagtaacaaa     60

ttcacctgcc ataatgatgc agagaggcaa ttttaggaac caaagaaaaa ctgttaagtg    120

tttcaattgt ggcaaagaag ggcacatagc caaaaattgc agggccccta ggaaaagggg    180

ctgttggaaa tgtgghaagg aaggam                                         206

<210> SEQ ID NO 37
<211> LENGTH: 60
<212> TYPE: DNA
<213> ORGANISM: Human immunodeficiency virus
<220> FEATURE:
<221> NAME/KEY: misc_feature
<222> LOCATION: (19)..(21)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t

<400> SEQUENCE: 37

aggtaacaaa tacrgctgnn ntaatgatgc agcgaaacaa ctttaagggt nncaaagaaa     60

<210> SEQ ID NO 38
<211> LENGTH: 60
<212> TYPE: DNA
<213> ORGANISM: Human immunodeficiency virus
<220> FEATURE:
<221> NAME/KEY: misc_feature
<222> LOCATION: (15)..(17)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 38

aagcaaataa tacannnaac ataatgatgc agagaaacaa ctttaaaggc ncctaanaag     60

<210> SEQ ID NO 39
<211> LENGTH: 60
<212> TYPE: DNA
<213> ORGANISM: Human immunodeficiency virus
```

-continued

<220> FEATURE:
<221> NAME/KEY: misc_feature
<222> LOCATION: (46)..(47)
<223> OTHER INFORMATION: n is a, c, g, or t

<400> SEQUENCE: 39
aagtaacacc accagctaac ataatgatgc agagaggcaa ttttanngga accaaagaaa 60

<210> SEQ ID NO 40
<211> LENGTH: 60
<212> TYPE: DNA
<213> ORGANISM: Human immunodeficiency virus
<220> FEATURE:
<221> NAME/KEY: misc_feature
<222> LOCATION: (46)..(47)
<223> OTHER INFORMATION: n is a, c, g, or t

<400> SEQUENCE: 40
aagtaacaca accagctacc ataatgatgc agagaggcaa ttttanngga accaaagaaa 60

<210> SEQ ID NO 41
<211> LENGTH: 60
<212> TYPE: DNA
<213> ORGANISM: Human immunodeficiency virus
<220> FEATURE:
<221> NAME/KEY: misc_feature
<222> LOCATION: (46)..(47)
<223> OTHER INFORMATION: n is a, c, g, or t

<400> SEQUENCE: 41
aagtaacaaa ttcacctgcc ataatgatgc agagaggcaa ttttanngga accaaagaaa 60

<210> SEQ ID NO 42
<211> LENGTH: 60
<212> TYPE: DNA
<213> ORGANISM: Human immunodeficiency virus
<220> FEATURE:
<221> NAME/KEY: misc_feature
<222> LOCATION: (46)..(47)
<223> OTHER INFORMATION: n is a, c, g, or t

<400> SEQUENCE: 42
aagtaacaaa ttcacctgcc ataatgatgc agagaggcaa ttttanngga accaaagaaa 60

<210> SEQ ID NO 43
<211> LENGTH: 60
<212> TYPE: DNA
<213> ORGANISM: Human immunodeficiency virus
<220> FEATURE:
<221> NAME/KEY: misc_feature
<222> LOCATION: (27)..(27)
<223> OTHER INFORMATION: n is a, c, g, or t

<400> SEQUENCE: 43
aattattaaa tgtttcaact gtggcangga gggacacyta gcaaaaaatt gcagggcccc 60

<210> SEQ ID NO 44
<211> LENGTH: 60
<212> TYPE: DNA
<213> ORGANISM: Human immunodeficiency virus

<400> SEQUENCE: 44
aattattaaa tgtttcaact gtggcaagga agggcactta gccagaaatt gcagggcccc 60

<210> SEQ ID NO 45
<211> LENGTH: 60
<212> TYPE: DNA

-continued

<213> ORGANISM: Human immunodeficiency virus
<220> FEATURE:
<221> NAME/KEY: misc_feature
<222> LOCATION: (23)..(25)
<223> OTHER INFORMATION: n is a, c, g, or t

<400> SEQUENCE: 45
gactgttaag tgtttcaatt gtnnndaaga agggcayata gccaaaaatt gcagggcccc 60

<210> SEQ ID NO 46
<211> LENGTH: 60
<212> TYPE: DNA
<213> ORGANISM: Human immunodeficiency virus

<400> SEQUENCE: 46
gactgttaag tgtttcaatt gbbbvaaaga agggcacata gccaaaaatt gcagggcccc 60

<210> SEQ ID NO 47
<211> LENGTH: 60
<212> TYPE: DNA
<213> ORGANISM: Human immunodeficiency virus

<400> SEQUENCE: 47
aactgttaag tgtttcaatt gtggcaaaga agggcacata gccaaaaatt gcagggcccc 60

<210> SEQ ID NO 48
<211> LENGTH: 60
<212> TYPE: DNA
<213> ORGANISM: Human immunodeficiency virus

<400> SEQUENCE: 48
aactgttaag tgtttcaatt gtggcaaaga agggcacata gccaaaaatt gcagggcccc 60

<210> SEQ ID NO 49
<211> LENGTH: 30
<212> TYPE: DNA
<213> ORGANISM: Human immunodeficiency virus
<220> FEATURE:
<221> NAME/KEY: misc_feature
<222> LOCATION: (26)..(28)
<223> OTHER INFORMATION: n is a, c, g, or t

<400> SEQUENCE: 49
taggddgddg ggttgttgga aatgtnnnaa 30

<210> SEQ ID NO 50
<211> LENGTH: 38
<212> TYPE: DNA
<213> ORGANISM: Human immunodeficiency virus

<400> SEQUENCE: 50
taggaaaaaa ggctgttgga aatgtggaaa ggaaggac 38

-continued

```
<210> SEQ ID NO 51
<211> LENGTH: 25
<212> TYPE: DNA
<213> ORGANISM: Human immunodeficiency virus

<400> SEQUENCE: 51

taggaadaag ggctgttgga aatgt                                   25


<210> SEQ ID NO 52
<211> LENGTH: 40
<212> TYPE: DNA
<213> ORGANISM: Human immunodeficiency virus

<400> SEQUENCE: 52

taggaaaaag ggctgttgga aatgtggtag ggaaggacac                   40


<210> SEQ ID NO 53
<211> LENGTH: 38
<212> TYPE: DNA
<213> ORGANISM: Human immunodeficiency virus

<400> SEQUENCE: 53

taggaaaagg ggctgttgga aatgtgghaa ggaaggam                     38


<210> SEQ ID NO 54
<211> LENGTH: 38
<212> TYPE: DNA
<213> ORGANISM: Human immunodeficiency virus

<400> SEQUENCE: 54

taggaaaagg ggctgttgga aatgtgghaa ggaaggam                     38
```